United States Patent
Wasden et al.

(10) Patent No.: US 7,736,321 B2
(45) Date of Patent: Jun. 15, 2010

(54) COMPUTER-ASSISTED DIAGNOSTIC HEARING TEST

(75) Inventors: Christopher L. Wasden, Sugar Land, TX (US); Kenneth R. Stott, Sugar Land, TX (US)

(73) Assignee: Tympany, LLC, The Woodlands, TX (US)

( * ) Notice: Subject to any disclaimer, the term of this patent is extended or adjusted under 35 U.S.C. 154(b) by 0 days.

(21) Appl. No.: 10/942,712

(22) Filed: Sep. 16, 2004

(65) Prior Publication Data

US 2005/0033193 A1    Feb. 10, 2005

Related U.S. Application Data

(63) Continuation-in-part of application No. 10/663,225, filed on Sep. 16, 2003, now Pat. No. 7,288,072, which is a continuation-in-part of application No. 10/439,958, filed on May 15, 2003.

(60) Provisional application No. 60/504,079, filed on Sep. 19, 2003.

(51) Int. Cl.
  *A61B 5/00* (2006.01)
(52) U.S. Cl. ...................................... 600/559
(58) Field of Classification Search ......... 600/300–301, 600/551, 559; 700/94
  See application file for complete search history.

(56) References Cited

U.S. PATENT DOCUMENTS

| | | | |
|---|---|---|---|
| 3,054,855 A | 9/1962 | Hyman | |
| 3,134,861 A | 5/1964 | Dempsey | |
| 3,221,100 A * | 11/1965 | Towne | 73/585 |
| 3,623,241 A | 11/1971 | Horner et al. | |
| 5,197,332 A | 3/1993 | Shennib | |
| 5,323,468 A | 6/1994 | Bottesch | |
| 5,645,074 A | 7/1997 | Shennib et al. | |
| 5,811,681 A | 9/1998 | Braun et al. | |
| 6,160,893 A | 12/2000 | Saunders et al. | |
| 6,168,563 B1 | 1/2001 | Brown | |

(Continued)

FOREIGN PATENT DOCUMENTS

GB    2351838 A    1/2001

(Continued)

OTHER PUBLICATIONS

International Search Report for PCT/US03/16200 dated Jul. 28, 2004.

(Continued)

*Primary Examiner*—Max Hindenburg
*Assistant Examiner*—Rene Towa
(74) *Attorney, Agent, or Firm*—Locke Lord Bissell & Liddell LLP

(57) ABSTRACT

Method and System are disclosed for a computer-assisted diagnostic hearing test. The computer-assisted diagnostic hearing test includes an ambient noise monitoring module configured to monitor an ambient noise in a surrounding environment, a patient information module configured to receive patient information and hearing related tests selections, and a pure tone threshold module configured to facilitate manual testing of a pure tone threshold test. The computer-assisted diagnostic hearing test further includes a speech reception threshold module configured to facilitate manual testing of a speech reception threshold test, and a speech discrimination module configured to facilitate manual testing of a speech discrimination test.

3 Claims, 8 Drawing Sheets

U.S. PATENT DOCUMENTS

| | | | |
|---|---|---|---|
| 6,201,875 B1 | | 3/2001 | Davis et al. |
| 6,319,207 B1* | | 11/2001 | Naidoo ..................... 600/559 |
| 6,322,521 B1* | | 11/2001 | Hou ........................... 600/559 |
| 6,331,164 B1 | | 12/2001 | Shaw et al. |
| 6,366,863 B1 | | 4/2002 | Bye et al. |
| 6,377,925 B1 | | 4/2002 | Greene et al. |
| 6,379,314 B1 | | 4/2002 | Horn |
| 6,396,930 B1 | | 5/2002 | Vaudrey et al. |
| 6,416,482 B1 | | 7/2002 | Braun et al. |
| 6,428,485 B1 | | 8/2002 | Rho |
| 6,447,461 B1 | | 9/2002 | Eldon |
| 6,496,585 B1* | | 12/2002 | Margolis ..................... 381/60 |
| 6,644,120 B1 | | 11/2003 | Braun et al. |
| 6,647,345 B2 | | 11/2003 | Bye et al. |
| 6,648,820 B1* | | 11/2003 | Sarel ........................... 600/300 |
| 6,674,862 B1 | | 1/2004 | Magilen |
| 6,730,041 B2 | | 5/2004 | Dietrich |
| 2001/0049480 A1 | | 12/2001 | John et al. |
| 2002/0016554 A1 | | 2/2002 | Iseberg |
| 2002/0026125 A1 | | 2/2002 | Leysieffer |
| 2002/0068986 A1 | | 6/2002 | Mouline |
| 2002/0076056 A1 | | 6/2002 | Pavlakos |
| 2002/0107692 A1 | | 8/2002 | Litovsky |
| 2002/0136365 A1 | | 9/2002 | D'Agri |
| 2002/0165466 A1* | | 11/2002 | Givens et al. ............... 600/559 |
| 2003/0072455 A1* | | 4/2003 | Johansen et al. ............. 381/60 |
| 2003/0083591 A1 | | 5/2003 | Edwards et al. |
| 2004/0006283 A1 | | 1/2004 | Harrison et al. |
| 2004/0039299 A1 | | 2/2004 | Harrison et al. |
| 2004/0049125 A1* | | 3/2004 | Nakamura ................. 600/559 |
| 2004/0064066 A1 | | 4/2004 | John et al. |
| 2004/0068200 A1 | | 4/2004 | Harrison et al. |
| 2004/0071295 A1 | | 4/2004 | Wasden et al. |
| 2004/0071296 A1 | | 4/2004 | Wasden et al. |
| 2004/0073134 A1 | | 4/2004 | Wasden et al. |
| 2004/0073135 A1 | | 4/2004 | Wasden et al. |
| 2004/0073136 A1 | | 4/2004 | Thorton et al. |
| 2004/0097826 A1 | | 5/2004 | Harrison et al. |
| 2004/0097839 A1 | | 5/2004 | Epley |
| 2004/0152998 A1 | | 8/2004 | Stott et al. |
| 2005/0033193 A1 | | 2/2005 | Wasden et al. |

FOREIGN PATENT DOCUMENTS

| | | |
|---|---|---|
| JP | 05030599 A | 2/1993 |
| NL | 8400196 | 8/1984 |
| WO | 8707464 A | 12/1987 |
| WO | WO9841973 | 9/1998 |
| WO | 0065983 A | 11/2000 |
| WO | WO0106916 | 2/2001 |
| WO | WO02062221 | 8/2002 |
| WO | 04104761 | 12/2004 |

OTHER PUBLICATIONS

International Search Report for PCT/US04/15329 dated Nov. 16, 2004.

International Search Report for PCT/US04/15328 dated Nov. 19, 2004.

Gelfand, S.A., *Essentials of Audiology*, 2d ed., Thieme Medical Publishers, Inc., 2001.

McCullough et al., *A multimedia approach for estimating speech recognition of multilingual clients*, AJA, Mar. 1994, pp. 19-22.

Matsuhira, Toshimasa, *Improved method of masking in pure tone audiometry—use of minimum level masking*, Practice Oto-Rhino-Laryngologica, 82:11; 1541-1540, 1989.

Smith, Brenda L. and Markides, Andreas, *Interaural attenuation for pure tones and speech*, British Journal of Audiology, 15:40 9-54, 1981.

Thornton, Aaron, *Computer-Assisted Audiometry and Technicians in a High-Volume Practice*, Nov. 1993 AJA, pp. 11-13.

Barry, S. Joseph, *Can Bone Conduction Thresholds Really Be Poorer Than Air?*, Nov. 1994 AJA, pp. 21-22.

M.S. Dean and F.N. Martin, *Insert Earphone Depth and the Occlusion Effect*, AJA, vol. 9, 159-0889, Sep. 5, 2000.

J.A. McCullough, R.H. Wilson, J.D. Birck and L.G. Anderson, *A Multimedia Approach for Estimating Speech Recognition of Multilingual Clients*, Mar. 1994 AJA, pp. 19-22.

R.H. Wilson and J.K. Antablin, *A Picture Identification Task as an Estimate of the Word-Recognition Performance of Nonverbal Adults*, Journal of Speech and Hearing Disorders, May 1980, vol. 45, No. 2.

International Search Report for PCT/US03/16180 dated Oct. 6, 2003.

Gerald A. Studebaker, et al., *Frequency-Importance and Transfer Functions for Recorded CID-W-22 Word Lists*, Journal of Speech and Hearing Research; Apr. 1991, pp. 427-438; vol. 34.

Aaron R. Thornton, et al., *Speech-Discrimination Scores Modeled as a Binomial Variable*, Journal of Speech and Hearing Research, Sep. 1978, pp. 507-518; vol. 21, No. 3.

Chris Haplin, Ph.D., et al., *The articulation index in clinical diagnosis and hearing aid fitting*, Current Opinion in Otalaryngology & Head and Neck Surgery, 1996, pp. 325-334; Rapid Science Publishers.

*The Audiology Primer for Students and Health Care Professionals*; Summer, 1997, pp. i-69; Department of Veterans Affairs.

Rogers, J., "Audiology Policy for Stenger Screening Test." Conwy & Denbighshire NHS Trust. Apr. 2002 [retrieved on Apr. 3, 2007]. Retrieved from the Internet: <URL:http://www.glanclwyd.demon.co.uk/audiology/clinprot/stengerscreeningpolicy.htm>, entire document.

European Supplementary Search Report for Corresponding European Patent Application EP04752359.2.

European Supplementary Search Report for European Patent Application No. 04752358.4, dated Apr. 2009.

* cited by examiner

COMPUTER-ASSISTED DIAGNOSTIC HEARING TEST

CROSS-REFERENCE TO RELATED APPLICATION

This application for patent claims the benefit of priority from, and hereby incorporates by reference, U.S. Provisional Patent Application Ser. No. 60/504,079, entitled "Computer-Assisted Diagnostic Hearing Test," and filed on Sep. 19, 2003, and is a continuation-in-part of U.S. patent application Ser. No. 10/663,225, entitled "User Interface for Automated Diagnostic Hearing Test," and filed on Sep. 16, 2003, now U.S. Pat. 7,288,072 which is a continuation-in-part of U.S. patent application Ser. No. 10/439,958, entitled "Automated Diagnostic Hearing Test," and filed on May 15, 2003, all of which are hereby incorporated by reference.

BACKGROUND OF THE INVENTION

1. Field of the Invention

This invention is directed in general to the field of audiology and in particular to a computer-assisted method and system of assessing and analyzing hearing loss.

2. Description of the Related Art

According to recent studies, over 20 million people in the United States alone have some degree of hearing loss. The number of people worldwide who have some degree of hearing loss is estimated to be much greater. Not surprisingly, many of these people are unaware that they have suffered a decrease in hearing capacity. The decreased hearing capacity may be due to several factors, including age, health, occupation, injury, and disease. This loss of hearing can lead to significant reduction in quality of life, impaired relationships, reduced access to employment and diminished productivity. Failure to treat the hearing loss may worsen the impact. According to the Better Hearing Institute, the annual cost in the United States in terms of lost productivity, special education, and medical care due to untreated hearing loss is approximately $56 billion. Much of this staggering cost can be reduced or prevented by early detection and treatment. Unfortunately, few people obtain regular and frequent hearing tests as a part of their routine healthcare due to the lack of a simple, convenient, and relatively inexpensive hearing test.

Traditionally, a hearing test is conducted in a clinical setting by a hearing health professional, such as an audiologist, who manually administers the hearing test. The hearing health professional controls an audiometer to produce a series of tones that each have a specific frequency and intensity. The term "intensity" as used herein refers to the amplitude of the tone and is usually stated in decibels (dB). The tones are then conducted through a transducer, such as earphones or ear inserts, to the patient in a quiet room or sound isolation booth. For each tone that is audible, the patient gestures or otherwise indicates that he has heard the tone. If the tone is not audible, the patient does not respond. The hearing health professional thereafter adjusts the intensity level of the tone in preset increments until the tone becomes audible to the patient. By repeating this process for several different tones and compiling the results, the hearing health professional is able to determine the extent of the hearing loss, if any.

An advantage of having a hearing health professional manually administer the hearing test is the hearing health professional can use his considerable training and experience during the test. For example, by simply talking to the patient and varying the loudness of his voice, the hearing health professional can determine an initial intensity level at which to start the tones and sounds. Furthermore, the hearing health professional can adapt the pace of the test as needed to accommodate a tired or uncooperative patient. More importantly, the hearing health professional can discern between false responses or guesses and responses that are legitimate. Finally, the hearing health professional can adjust the results of the hearing test as needed to reflect extenuating circumstances or problems, such as excessive ambient noise, equipment limitations, and other similar factors.

Traditional audiometers and other hearing test equipment, however, can be awkward and difficult to use. For example, traditional audiometers typically require the hearing health professional to manually turn knobs and adjust dials. Test information such as frequency and intensity level must typically be read from needle gauge readouts. Moreover, the hearing health professional must manually perform many aspects of the hearing test, including plotting the hearing thresholds and setting the masking levels. All of this is not only inefficient and time consuming, but also conveys a "low-tech" look and feel that may instill doubt in the patient's mind regarding the accuracy of the test.

Accordingly, what is needed is a hearing test that can be administered by a hearing health professional without the shortcomings of the traditional hearing test. Specifically, what is needed is a user friendly hearing test that can be administered by the hearing health professional with the aid of a computer.

SUMMARY OF THE INVENTION

The present invention is directed to a computer-assisted diagnostic hearing test. The computer-assisted diagnostic hearing test includes an ambient noise monitoring module configured to monitor an ambient noise in a surrounding environment, a patient information module configured to receive patient information and hearing related tests selections, and a pure tone threshold module configured to facilitate manual testing of a pure tone threshold test. The computer-assisted diagnostic hearing test further includes a speech reception threshold module configured to facilitate manual testing of a speech reception threshold test, and a speech discrimination module configured to facilitate manual testing of a speech discrimination test.

In general, in one aspect, the invention is directed to a computer-assisted method of presenting a diagnostic hearing test. The method comprises the steps of displaying a graphical set of controls for the diagnostic hearing test, the controls controlling various aspects of the diagnostic hearing test, and allowing a user to specify one or more aspects of the diagnostic hearing test using the graphical set of controls. The method further comprises the steps of presenting a hearing test signal to a transducer in accordance with the graphical controls as specified by the user and storing a patient response to the hearing test signal as indicated by the user via the graphical controls. A report of the result of the diagnostic hearing test may then be generated for the user.

In general, in another aspect, the invention is directed to a computer-based system for conducting a diagnostic hearing test. The system comprises a display screen, a central processing unit configured to control the display screen, a transducer for receiving hearing test signals from the central processing unit, and a storage unit connected to the central processor. The storage unit stores computer-readable instructions for causing the central processing unit to display a graphical set of controls for the diagnostic hearing test on the display screen, the controls controlling various aspects of the diagnostic hearing test. The computer-readable instructions further causes the central processing unit to allow a user to specify one or more aspects of the diagnostic hearing test using the graphical set of controls and to present a hearing test signal to the transducer in accordance with the graphical controls as specified by the user. The patient response to the hearing test signal, as indicated by the user, is then stored on the storage unit and a report of the result of the diagnostic hearing test is generated for the user.

In general, in yet another aspect, the invention is directed to a multimedia graphical user interface for a diagnostic hearing test. The user interface comprises an ambient noise module for graphically displaying an ambient noise level for the diagnostic hearing test, including an intensity level for one or more frequency components of the ambient noise. The user interface further comprises a patient information module for allowing a user to enter patient information and to select which hearing test and which ear to test for the patient. Also included is a pure tone module for allowing the user to manually conduct a pure tone threshold test, including selecting an intensity level and frequency for a pure tone signal to be presented to the patient. A speech reception module allows the user to manually conduct a speech reception threshold test, including recording patient responses to the speech reception threshold test, and a speech discrimination module allows the user to manually conduct a speech discrimination test, including recording patient responses to the speech discrimination test.

BRIEF DESCRIPTION OF THE DRAWINGS

A better understanding of the invention may be had by reference to the following detailed description when taken in conjunction with the accompanying drawings, wherein.

DETAILED DESCRIPTION OF THE INVENTION

Figure 1:
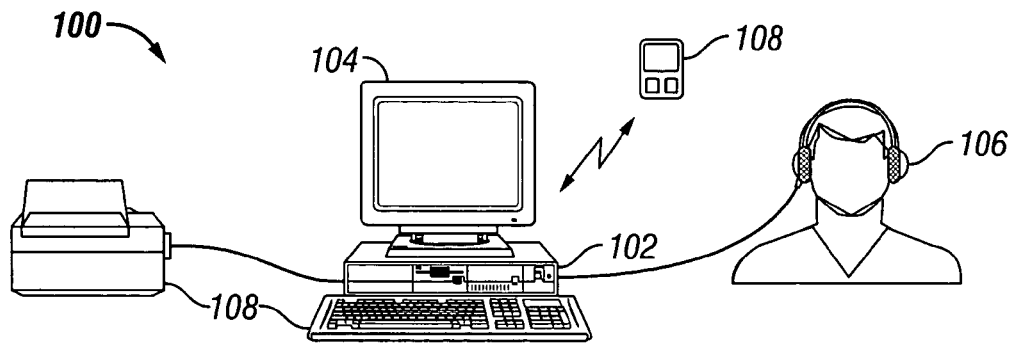
FIG. 1 illustrates an exemplary system for providing a computer-assisted hearing test according to embodiments of the invention.

Following is a detailed description of the invention with reference to the drawings wherein reference numerals for the same or similar elements are carried forward. It should be noted that unless otherwise indicated, the design and layout of the various features shown in the drawings, including the size, shape, color (or lack thereof), location, and arrangement of the various fields, checkboxes, text boxes, graphics, functional modules, and other information, are provided for illustrative purposes only, and the invention is not to be limited to any particular design or layout.

As mentioned above, the present invention is directed to computer-assisted diagnostic testing of a patient's hearing. The computer-assisted diagnostic hearing test uses computer-based hearing test equipment that include an intuitive, user-friendly multimedia interface for facilitating performance of the various hearing related tests. The hearing related tests can be controlled and performed manually, or the hearing health professional can choose to let certain aspects of the tests be controlled and performed automatically. The results of the tests are generated automatically by the computer-assisted diagnostic hearing test when the hearing related tests are completed.

Referring now to FIG. 1, a system 100 is shown for providing computer-assisted hearing tests according to embodiments of the invention. The system 100 has three main modules, namely, a computer 102, and a display screen 104, and at least one transducer 106. Other modules of the system 100 that may be present include a tympanometer, keyboard, mouse, printer, paging system, and the like (indicated generally at 108). The paging system may be any suitable paging technology that uses one or more pagers 108 for alerting an operator. The one or more pagers 108 preferably can display text messages for informing the operator of the nature of the alert. Other types of paging system may also be used without departing from the scope of the invention (e.g., Internet based paging systems).

The computer 102 may be any suitable computer, from a desktop PC to a high-end workstation, as the particular type/model/brand of computer is not overly important to the practice of the invention. The display screen 104 may likewise be any suitable display screen, from a CRT to an LCD, as the particular type/model/brand of display screen is not overly significant for purposes of the present invention. In some embodiments, however, a touchscreen monitor may be easier to use than conventional CRT or LCD display screens in terms of the physical interaction between the patient and the automated hearing test.

As for the transducer 106, this module may be an ear insert, earphones, and the like for air conduction. For bone conduction, the transducer 106 may be a vibrator or other similar devices. In some cases, the transducer 106 may be mounted on a headset worn by the patient. Usually, a separate transducer is used for air conduction versus bone conduction and the transducers are swapped as need during the hearing test. Preferably, the bone conduction transducer is arranged in such a way as to allow testing of either ear without moving the transducer and without interfering with the air conduction transducer. In some embodiments, both the air conduction transducer and the bone conduction transducer are combined in a single unit. An example of such a combined unit is described in U.S. patent application Ser. No. 10/438,751, entitled "Apparatus for Bone Conduction Threshold Hearing Test," which is hereby incorporated by reference.

Figure 2:
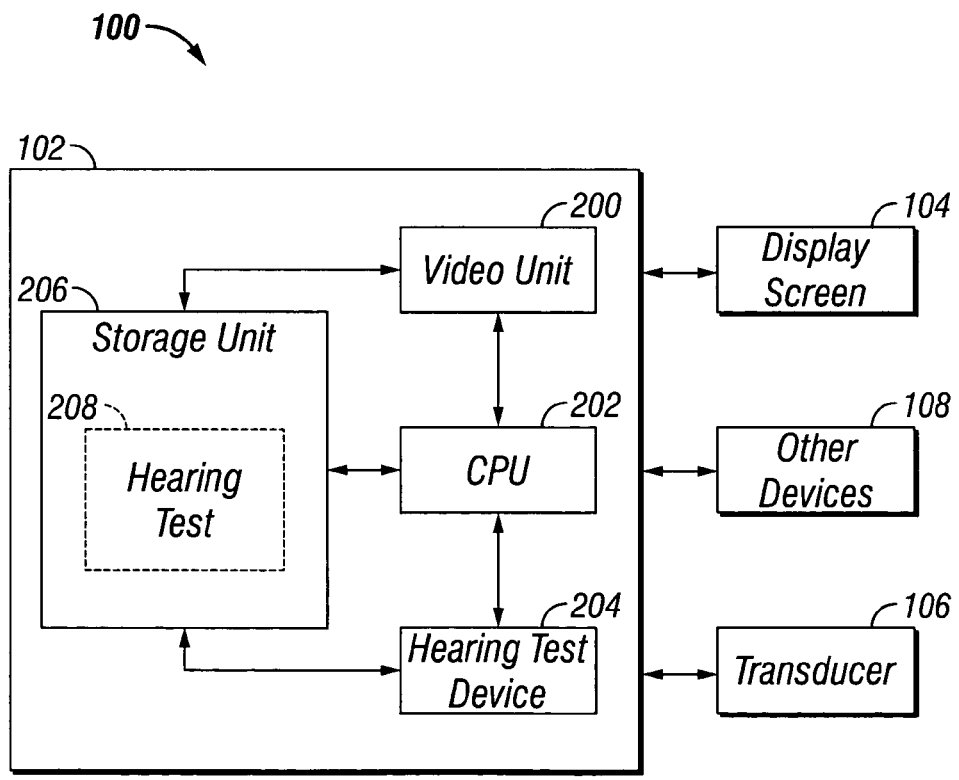
FIG. 2 illustrates a block diagram of the system for providing a computer-assisted diagnostic hearing test according to embodiments of the invention.

FIG. 2 illustrates the system 100 in block diagram form. As can be seen, the computer 102 has a number of functional modules, including a video unit 200, a central processing unit 202, a hearing test device 204, and a storage unit 206. These modules are well-known in the computer art and will therefore be described only briefly here. In general, the video unit 200 provides the video signals that are displayed as images on the display screen 104. In some embodiments, the video unit 200 may be any one of several commercially available video cards. The central processing unit 202 is responsible for the overall operation of the computer 102, including execution of the operating system and any software applications residing on the computer 102. In some embodiments, the central processing unit 202 may be any one of several commercially available microprocessors. The hearing test device 204 may comprise any or all of an audiometer, an otoacoustic emission test device, a tympanometer, a masking noise generator, or other hearing test devices. In some embodiments, the hearing test device 204 may be one or more electronic circuit boards within the computer 102 for performing the functionality of such test devices. Alternatively, the hearing test device 204 may be a separate unit that is external to the computer 102. The storage unit 206 provides long-term and temporary (i.e., caching) storage for the software and data that are used by the computer 102 and may include one or more of, for example, a hard drive, main memory, removable storage (e.g., CD-ROM, floppy disk), and the like.

In some embodiments, the storage unit 206 also stores a hearing test 208. More specifically, the storage unit 206 stores a computer-readable version of the hearing test 208 that can be executed by the computer 102. During execution, a portion of the hearing test 208 may be temporarily loaded from, for example, the hard disk and into the main memory modules of the storage unit 206. In addition to the stand-alone arrangement, it is also possible to execute the hearing test 208 from a network. For example, the hearing test 208 may be stored on a server computer (not expressly shown) that is accessible to several client computers. This arrangement has an advantage in that updates to the hearing test 208 may be quickly and easily implemented for all client computers. Other environments for executing the hearing test 208 may also be used without departing from the scope of the invention.

Figure 3:
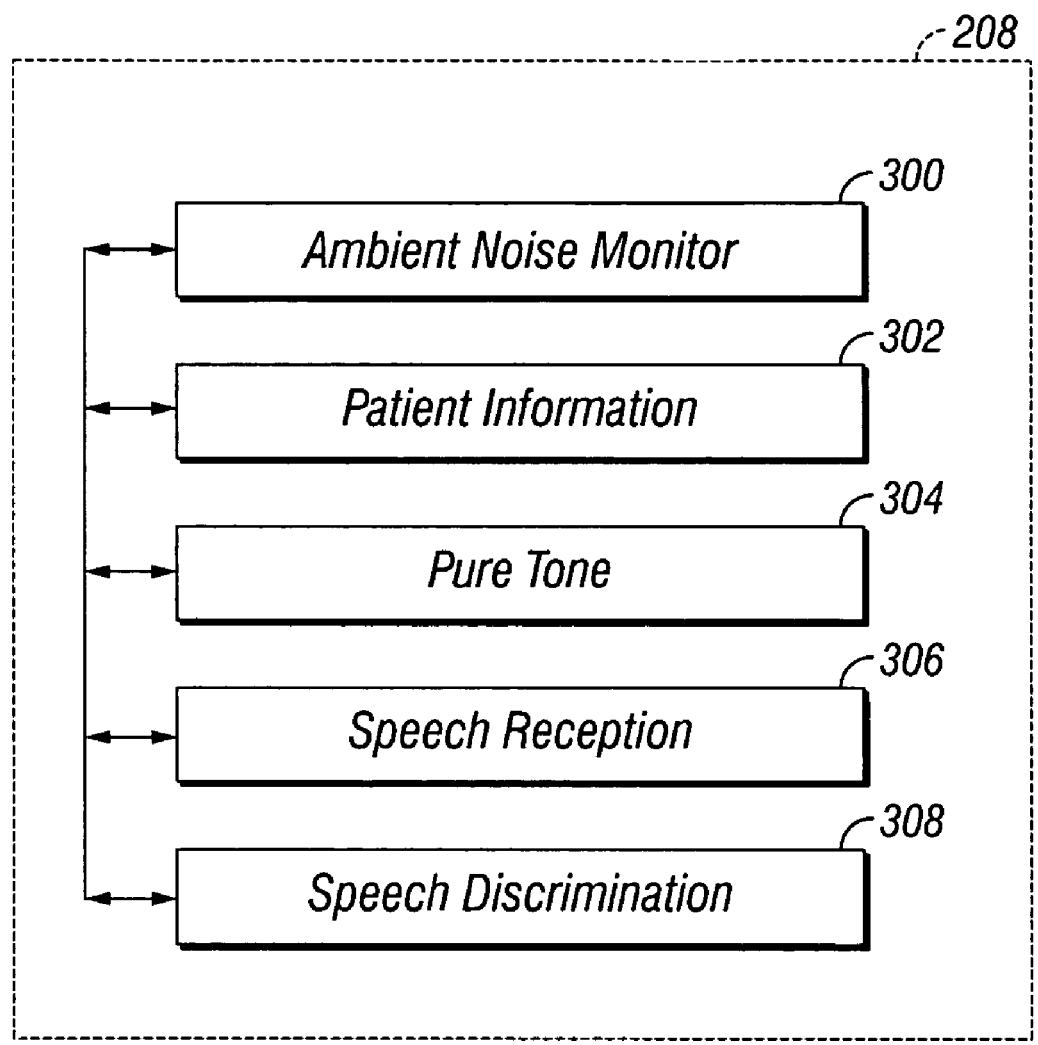
FIG. 3 illustrates an exemplary computer-assisted diagnostic hearing test according to embodiments of the invention.

FIG. 3 shows an exemplary implementation of the hearing test 208. As can be seen, the hearing test 208 has a number of functional modules, including an ambient noise monitoring module 300, a patient input module 302, a pure tone threshold module 304, a speech reception threshold module 306, and a speech discrimination module 308. The various functional modules are typically executed in sequence as the automated hearing test progresses, but any functional module can be executed before, during, or after execution of any other functional module as needed. Interaction with the hearing test 208 may be accomplished using any suitable input device, for example, a mouse, keyboard, separate dedicated response button, or using a touchscreen display unit. Where a touchscreen display unit is used, the hearing test 208 may display a graphical keyboard (in addition to or instead of a conventional keyboard) from which the operator and/or patient may select alphanumeric characters as needed. Following is a description of the various modules of the hearing test 208.

Figure 4:
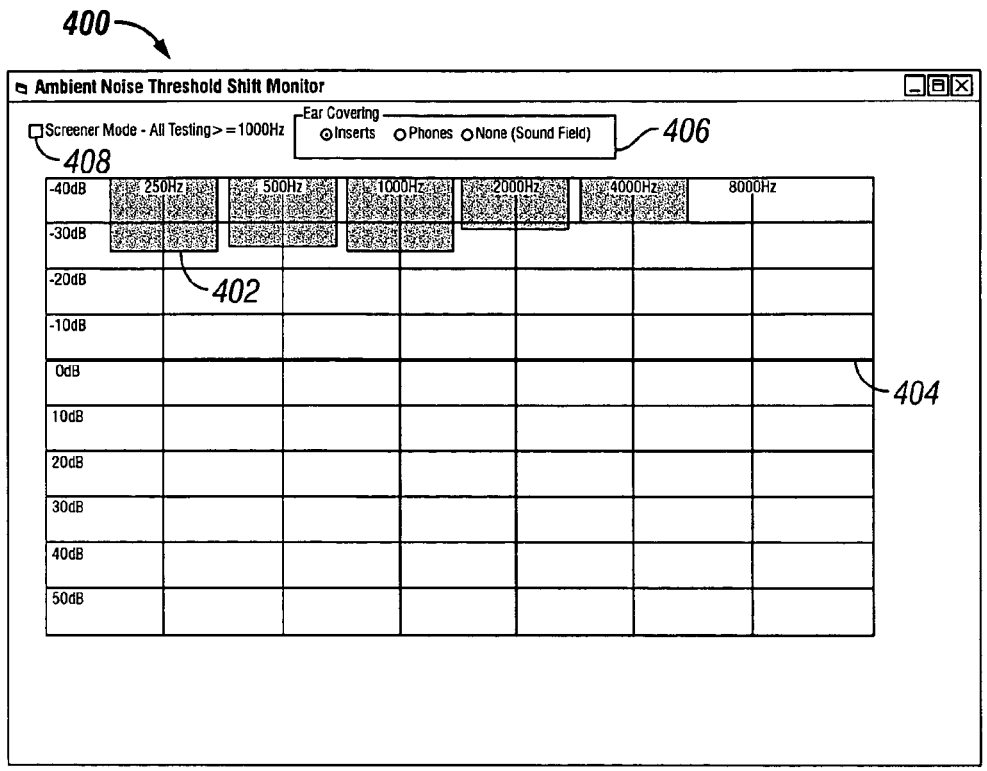
FIG. 4 illustrates an exemplary implementation of an ambient noise monitoring module of the computer-assisted diagnostic hearing test.

Referring now to FIG. 4, an exemplary implementation of the ambient noise monitoring module 300 is shown. The function of the ambient noise monitoring module is to monitor the ambient noise present in the surrounding environment. In some embodiments, the ambient noise monitoring module 300 includes an ambient noise screen 400. The ambient noise screen 400 has a chart that indicates the amount of ambient noise present in the environment. The intensity of the ambient noise is indicated along the vertical axis, and the frequencies of the ambient noise is indicated along the horizontal axis. A plurality of bars (one of which is shown at 402) represents the levels of intensity for the frequency components of the ambient noise present. The ambient noise screen 400 also includes an acceptable level indicator 404 that indicates the acceptable level of ambient noise according to, for example, the ANSI standard. Usually, any ambient noise component that exceeds the acceptable level has to be noted or otherwise highlighted in the test results for that frequency. A source indicator 406 indicates the particular source from which the ambient noise is being measured. For example, the source indicator 406 may indicate that the ambient noise is being measured from an insert in the patient's ear, from headphones over the patient's ear, or simply from an uncovered microphone. In some embodiments, the ambient noise screen 400 also includes an option 408 for testing only frequencies greater than or equal to, for example, 1 kHz.

Figure 5:
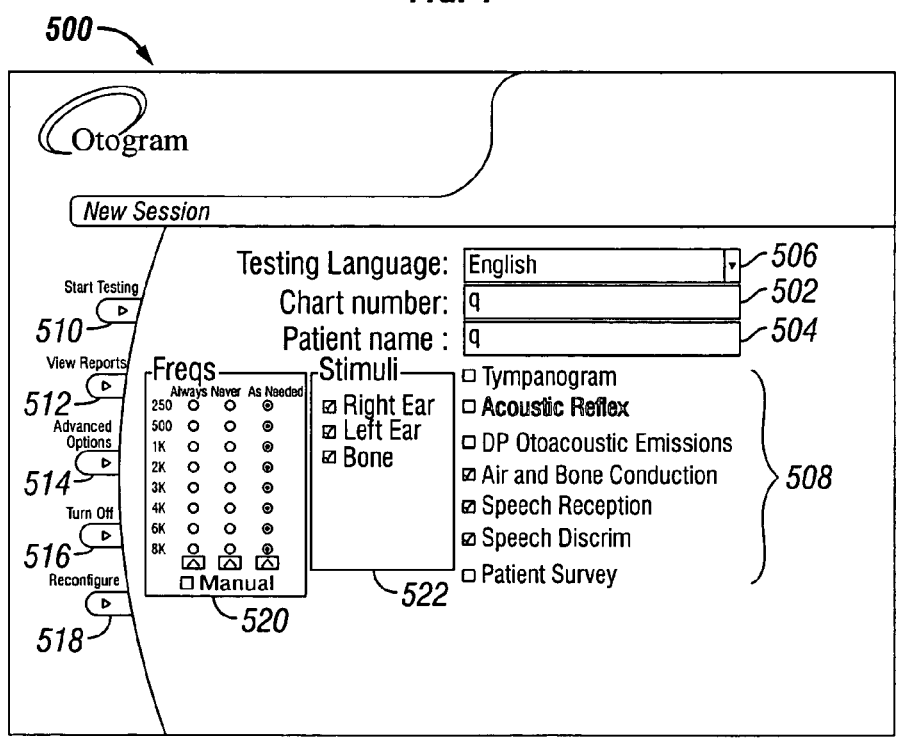
FIG. 5 illustrates an exemplary implementation of a patient information module of the computer-assisted diagnostic hearing.

FIG. 5 illustrates an exemplary implementation of the patient information module 302. The function of this module is to allow the hearing health professional to enter information about the patient and to select which hearing related test to be performed. In some embodiments, the patient information module 302 accomplishes the above function by providing the hearing health professional with a new session screen 500. The new session screen 500 may include a chart number field 502 for entering the patient's chart number and a patient name field 504 for entering the patient's name. This information, along with the date and possibly other information, may be used to store and subsequently retrieve the results of any test session. In addition, because the automated hearing test is capable of testing in multiple languages (e.g., English, Spanish, French, etc.), in some embodiments, the new session screen 500 may include a field 506 for selecting which language to be used to test the patient. The new session screen 500 may also include a plurality of checkboxes 508 for selecting which hearing related tests will be performed for the patient. For example, the new session screen 500 may include a checkbox for selecting a tympanogram test, an acoustic reflex test, and a distortion product (DP) otoacoustic emission test. Also available for selection are an air and bone conduction test, a speech reception test, and a speech discrimination test. Selecting a patient survey allows the automatic hearing test to gather certain hearing related information about the patient that can be used by the hearing health professional to diagnose and recommend treatment.

A plurality of buttons 510, 512, 514, 516, and 518 along the left side of the new session screen 500 allows the hearing health professional to initiate a number of tasks, such as starting testing, viewing reports, accessing advanced options, turning off testing, and reconfiguring the tests. In particular, the advanced options button 514 allows the hearing health professional to choose from a number of advanced options, including manual testing of the patient. In one example, pressing the advanced options button 514 brings up a box 520 that lists the frequencies from which the hearing health professional may choose to manually test. He may choose to test one or more of these frequencies always, never, or as needed. The advanced options button 514 also brings up a stimuli selection box 522 that allows the hearing health professional to select whether to test the right ear, left ear and/or bone conduction.

Figure 6:
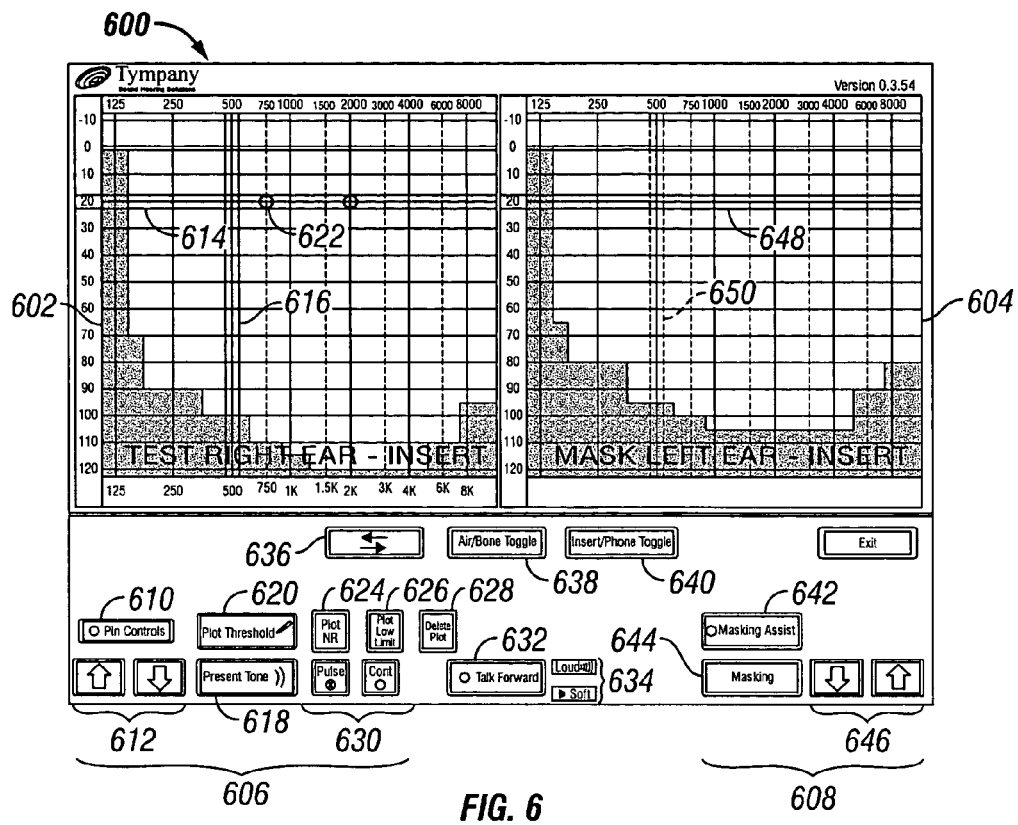
FIG. 6 illustrates an exemplary implementation of a pure tone threshold module of the computer-assisted diagnostic hearing test.

Testing begins with the pure tone threshold test, if selected. FIG. 6 illustrates an exemplary implementation of the pure tone threshold module 304 of the computer-assisted hearing test. The function of this module is to allow the hearing health professional to manually test the patient's ability to hear at various frequencies. To this end, in some embodiments, the pure tone threshold module 304 includes a pure tone test screen 600 that allows the hearing health professional to control various aspects of the pure tone threshold test. The pure tone test screen 600 also allows the hearing health professional to view the results of the test in real time as they occur.

Included in the pure tone test screen 600 is a test chart 602 for displaying the results of the ear being tested and a mask chart 604 for displaying the masking, if any, being applied to the non-test ear. A set of test controls 606 allows the hearing health professional to control the pure tone testing, while a set of mask controls 608 allows the hearing health professional to control the masking. In some embodiments, the test chart 602 and the mask chart 604 switch sides on the display unit depending on the ear being tested. For example, when the right ear is being tested, the test chart 602 appears on the left side and a mask chart 604 appears on the right side. When the left ear is being tested, the two charts 602 and 604 switch sides. In some embodiments, the test controls 606 and the mask controls 608 follow their respective charts 602 and 604 and switch sides accordingly. In other embodiments, it is possible to pin down the controls 606 and 608 by selecting a pin controls button 610.

The test controls 606 include a plurality of control buttons that lets the hearing health professional control the various aspects of the pure tone threshold test. For example, the test controls 606 include a tone intensity level controller 612 that allows the hearing health professional to adjust the intensity level of the tone being tested. Although it is implemented here as "up" and "down" buttons, the tone intensity level controller 612 may also be implemented using some other functional mechanism. A tone intensity level bar 614 indicates the current tone intensity level, and a tone frequency bar 616 indicates the current frequency of the tone. The hearing health professional may adjust the tone frequency by clicking or touching the numerical value of the desired frequency, or by dragging the vertical bar 616. Pressing a present tone button 618 causes a tone to be presented to the patient via his transducer at the set frequency and intensity level. The hearing health professional then waits to see if the patient has heard the tone. If the patient did not hear the tone, then the hearing health professional may increase the intensity level using the intensity level controller 612. If the patient indicates that he has heard the tone, then the hearing health professional may press a plot threshold button 620 to mark the frequency and the intensity level of the tone. An example of such a mark is shown at 622. If, however, the hearing health professional has increased the intensity level to the maximum level and the patient still has not heard the tone, then the hearing health professional may press a plot no response button 624 to mark on the chart 602 that there was no response at or above that frequency and intensity level. If, on the other hand, the hearing health professional has lowered the intensity level to the minimum level and the patient can still hear the tone, then the hearing health professional may press a plot low limit button 626 to mark on the chart 602 that the patient can hear at or below that frequency and intensity level. If the hearing health professional decides that he wishes to erase a mark, then he may press the delete plot button 628 to remove that mark.

A left/right toggle button 636 switches the testing between the left and right ears. An air/bone toggle button 638 toggles the testing between air conduction and bone conduction testing. If air conduction is used, an insert/phones button 640 toggles between an insert type transducer and a headphones type transducer. In some embodiments, the ear being tested and the transducer type being used, including bone conduction, is indicated (e.g., textually) in the test chart 602 and mask chart 604.

In some embodiments, the mask controls 608 include a masking assist button 642. Pressing this button engages the automatic masking feature of the hearing test 208. This feature automatically determines whether masking should be turned on for the non-test ear and also sets the masking intensity level. For more information regarding the automatic masking feature, the reader is referred to, for example, U.S. patent application Ser. No. 10/439,958, entitled "Automated Diagnostic Hearing Test," filed on May 15, 2003, mentioned above and incorporated herein by reference. Masking may also be controlled manually by the hearing health professional via a masking button 644. Pressing this button turns masking on for the non-test ear, after which the hearing health professional may adjust the intensity level using the masking intensity level controller 646. A masking intensity level bar 648 indicates the current masking intensity level, and a masking frequency bar 650 indicates the frequency of the current masking. Note that in some cases the frequency of the masking may track the frequency of the tone and, therefore, the masking frequency bar 650 is shown here with dashed lines.

Figure 7A:
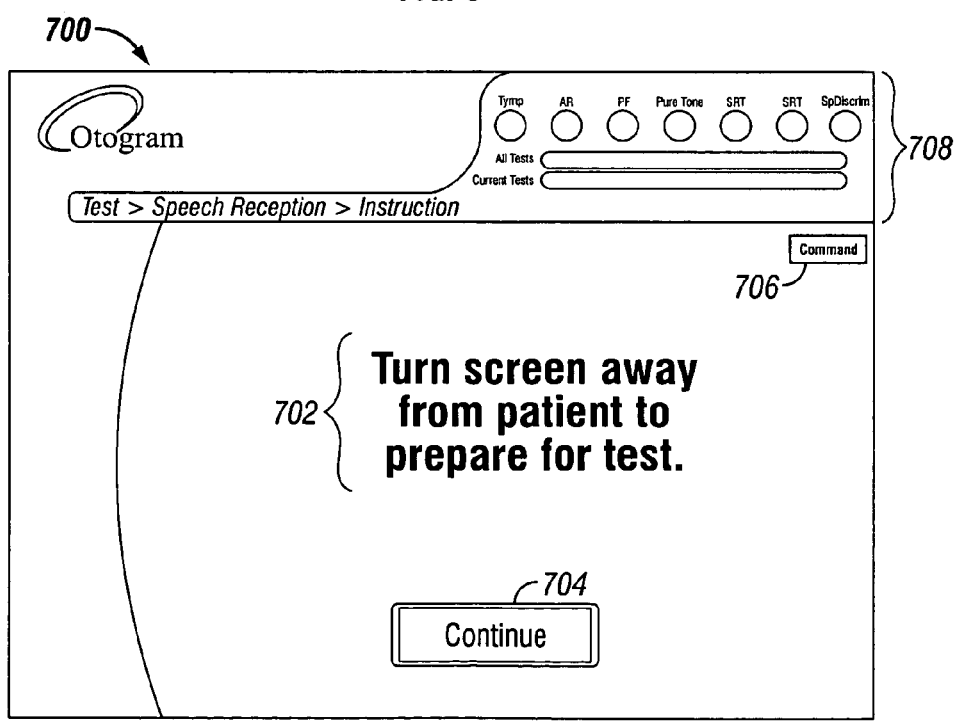
FIGS. 7A-7C illustrate an exemplary implementation of a speech reception threshold module of the computer-assisted diagnostic hearing test.
Figure 7B:
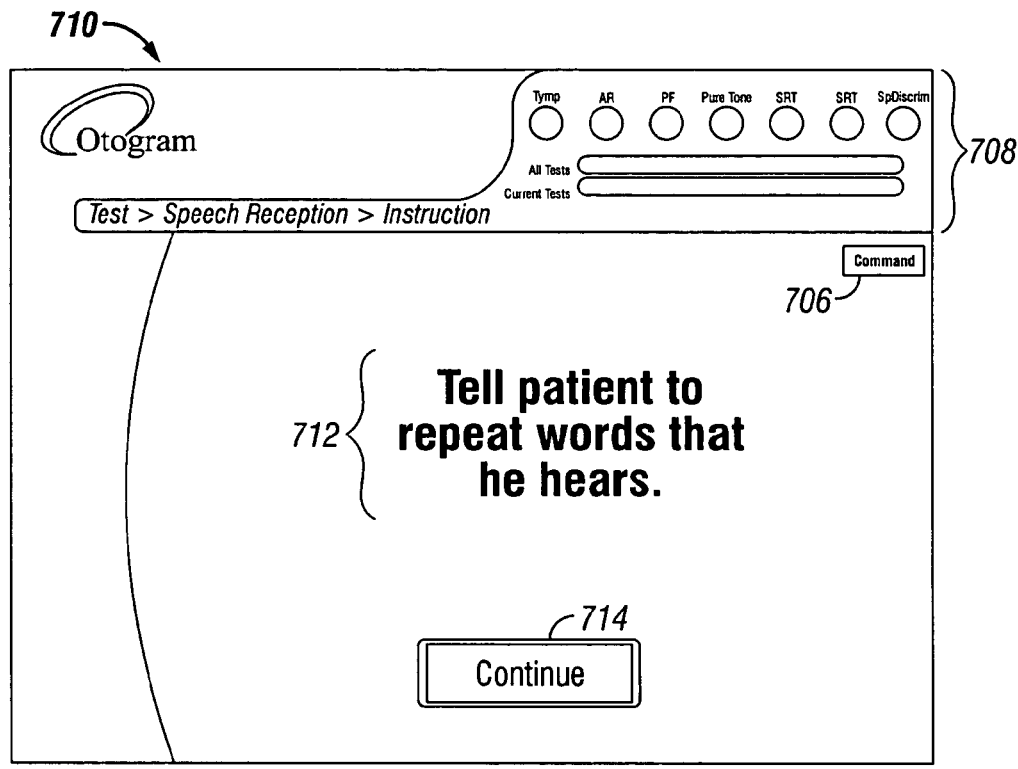
Figure 7C:
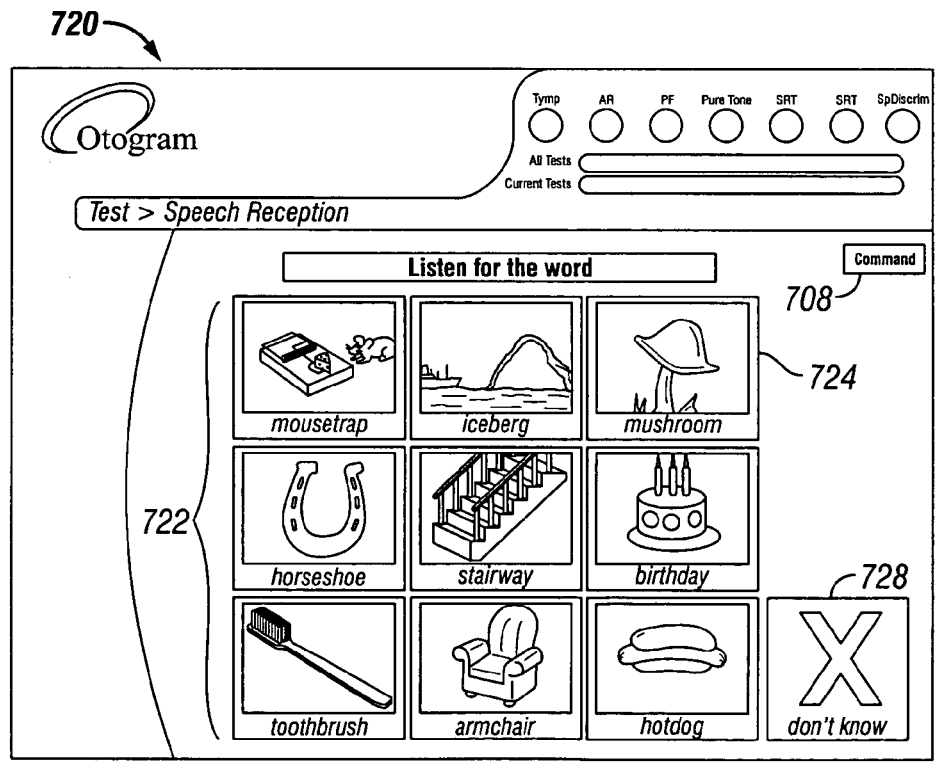
Figure 8A:
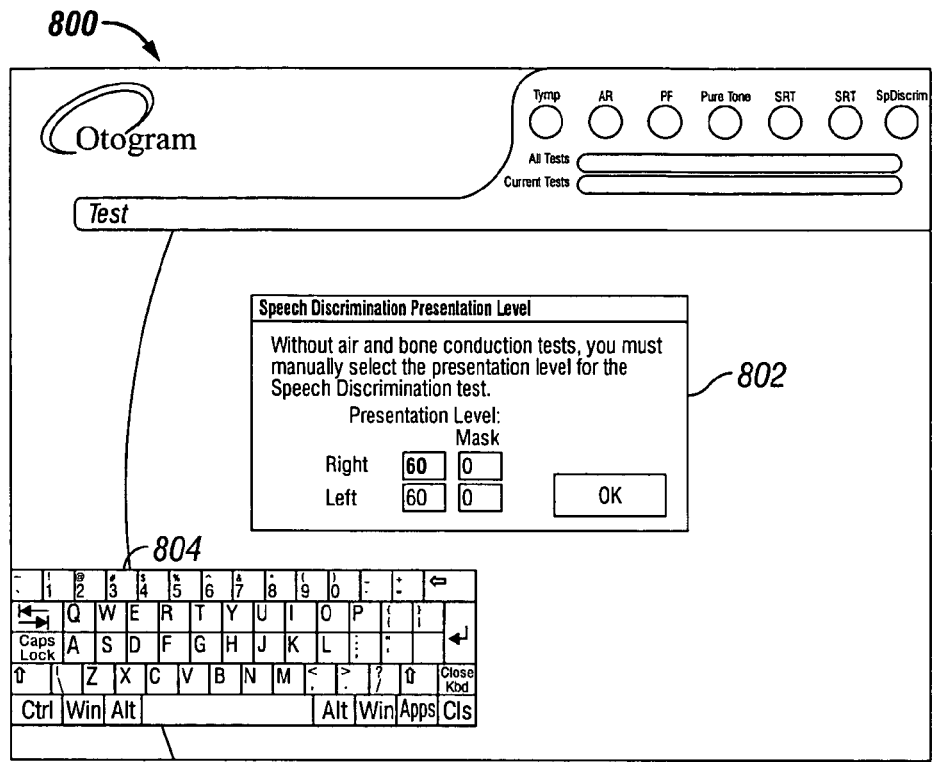
FIGS. 8A-8D illustrate an exemplary implementation of a speech discrimination module of the computer-assisted diagnostic hearing test.
Figure 8B:
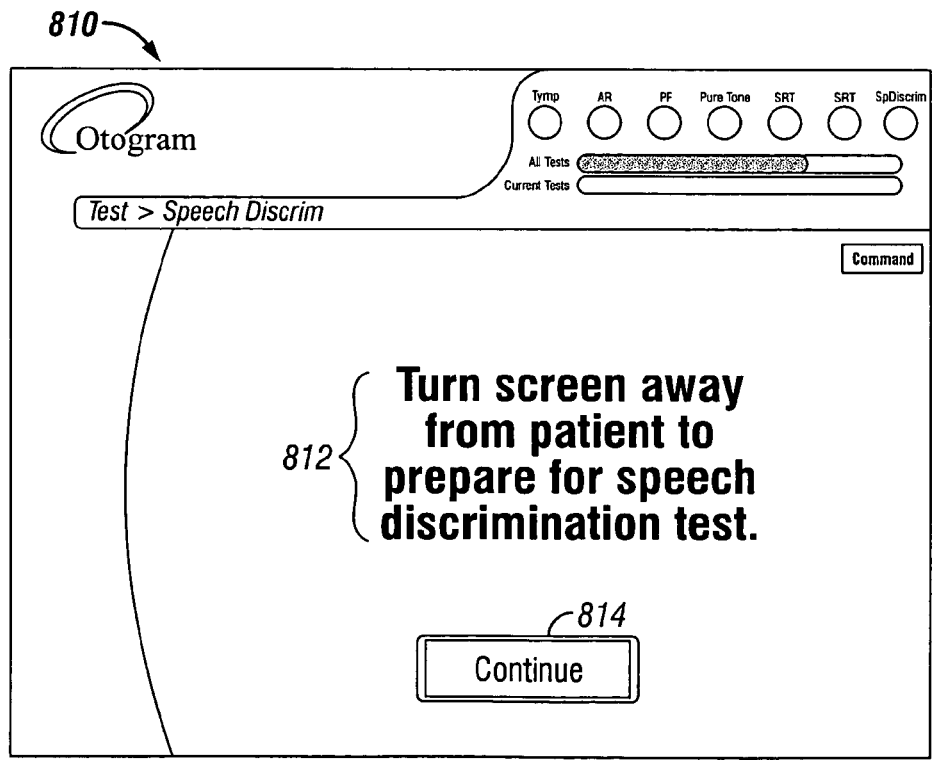
Figure 8C:
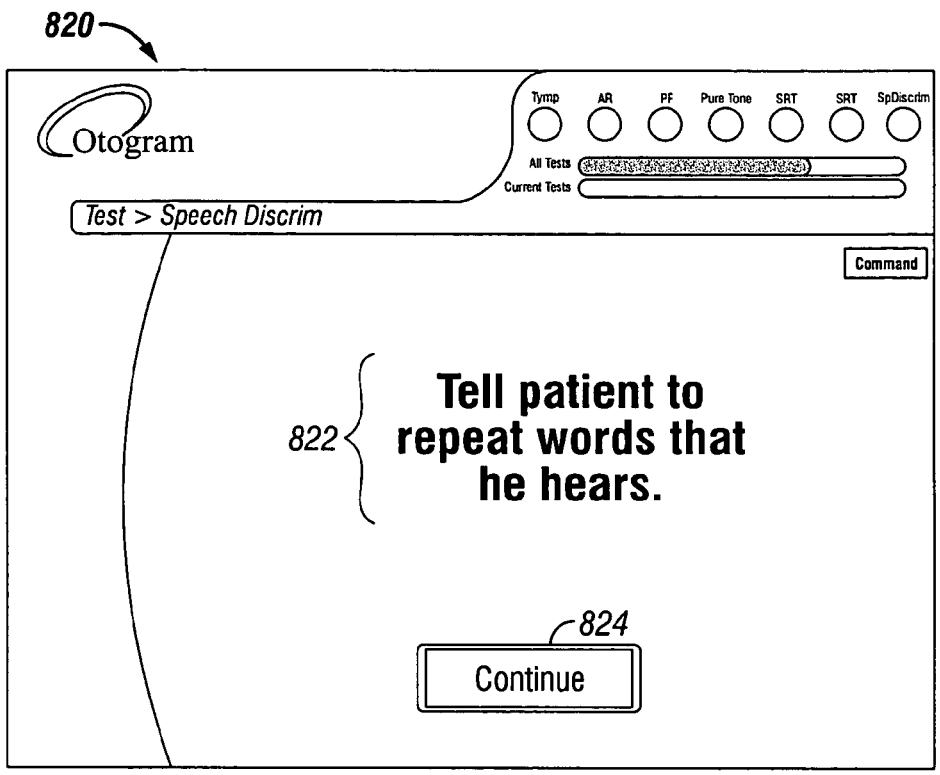
Figure 8D:
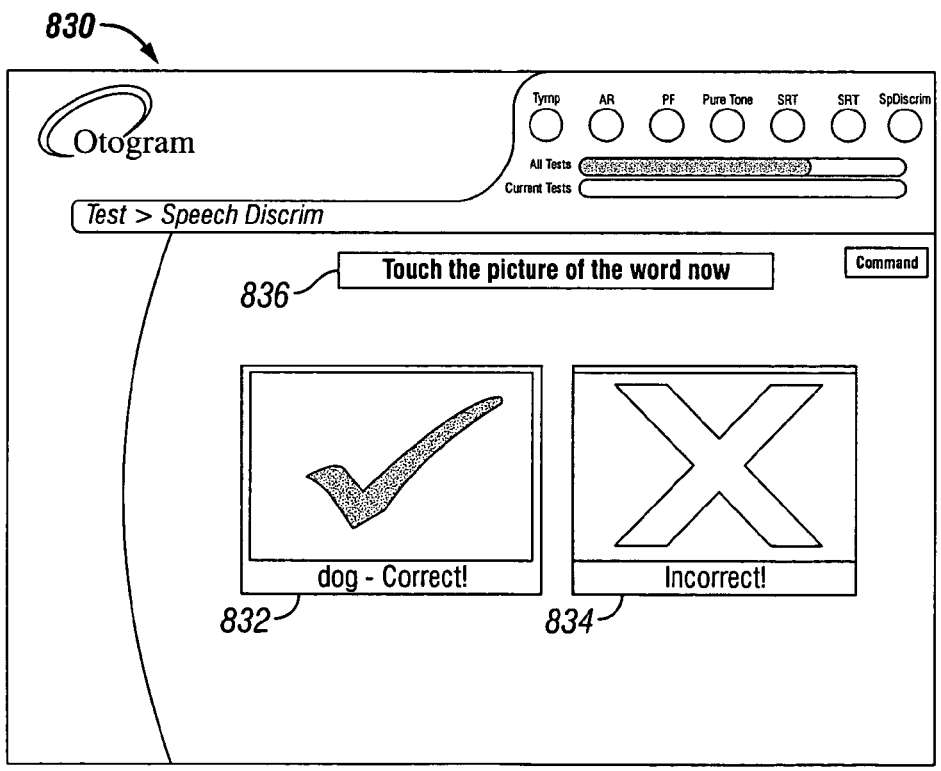

FIGS. 7A-7C illustrate an exemplary implementation of the speech reception threshold module 306. The function of this module is to facilitate manual testing of the patient's speech reception threshold. During the test, the speech reception threshold module 306 will present various words one at a time and at various intensity levels in the patient's transducer. The patient is then suppose to verbally repeat the word. Scoring is done by the hearing health professional via the speech reception threshold module 306. The words that are presented are selected from a predefined group of words. If the patient is unaware of this fact, then the test is considered an "open set" test because essentially any answer is possible. If the patient is aware of this fact and knows what words are available, then the test is considered a "closed set" test.

In some embodiments, the speech reception threshold module 306 begins with an instruction screen 700. The instructions screen 700 includes a set of instructions 702 that, among other things, instructs the hearing health professional to turn the display unit away from the patient. Turning the display unit away from the patient has the effect of converting an otherwise closed set test into an open set test because the patient cannot see the predefined group of words. The hearing health professional may, of course, inform the patient of the predefined group of words, in which case the test will become a closed set test. An acknowledgment button 704 may be pressed to indicate compliance with the instructions 702 and a command button 706 brings up various commands that are appropriate at this point (e.g., pause, exit, etc.). The progress of the test is indicated by a progress indicator 708. A second instructions screen 710 includes a set of instructions 712 that instructs the hearing health professional to tell the patient that he should repeat the words that he hears. Another acknowledgment button 714 may be pressed to indicate compliance with the second set of instructions 712, after which testing may begin.

As each word is presented to the patient, a speech reception screen 720 displays the predefined group 722 from which one of the words 724 is presented. Preferably, the words that are used are compound words with two distinct syllables. For languages where no such words are available, appropriate substitutes may be made. The speech reception threshold module 306 verbally presents the words to the patient one at a time, randomly, and at decreasing intensity levels, with no emphasis on any syllable. If the patient repeats the right word, then the hearing health professional may mark a correct answer by clicking or pressing on that word. In some embodiments, each word may be accompanied by a picture for that word, and the hearing health professional may press or click on the picture instead. If the patient repeats the wrong word or does not answer, then the hearing health professional may mark an incorrect answer by pressing or clicking a wrong answer button 728. The test is concluded automatically by the speech reception threshold module 306 when it determines that a threshold has been reached. In some embodiments, this threshold may be determined as the intensity level at which the patient can correctly identify 50% of words.

FIGS. 8A-8D illustrate an exemplary implementation of the speech discrimination module 308 of the hearing test 208. The function of the speech discrimination module 308 is to facilitate manual testing of the patient's ability to discriminate between words. The speech discrimination test, unlike the pure tone threshold and speech reception threshold tests, does not test for the softest level the patient can hear. Rather, the speech discrimination test checks to see how well the patient is able to discern words. Therefore, each word is presented at an intensity level at which the patient is most likely to hear the word. The particular words that are presented are single syllable words chosen randomly from a fairly large group of words and, therefore, the test is essentially an open set test.

The intensity level at which the words are presented is determined largely from the results of the pure tone threshold tests. For more information regarding the determination of the intensity level for the speech discrimination test, the reader is referred to, for example, U.S. patent application Ser. No. 10/439,958, entitled "Automated Diagnostic Hearing Test," filed on May 15, 2003, mentioned above and incorporated herein by reference. If the pure tone threshold tests has not been performed for the patient, then the speech discrimination module 308 informs the hearing health professional of this fact using a presentation level screen 800. The presentation level screen 800 explains to the hearing health professional that without the pure tone air and bone conduction test, the presentation level for the speech discrimination test must be manually set. A plurality of fields in the box 802 allows the hearing health professional to fill in the values to be used for the presentation level. In some embodiments, an on-screen keyboard 804 may be used to fill in the needed information.

After the presentation level has been determined, the speech discrimination module 308 provides an instruction screen 810. The instructions screen 810 includes a set of instructions 812 that instructs the hearing health professional to turn the display unit away from the patient. An acknowledgment button 814 may be pressed to indicate compliance with the instructions 812. A second instructions screen 820 includes a set of instructions 822 that instructs the hearing health professional to tell the patient that he should repeat the words that he hears. An acknowledgment button 824 may be pressed to indicate compliance with the second set of instructions 822, after which the test may begin.

As each word is presented to the patient, a speech discrimination screen 830 displays a correct answer box 832 and a wrong answer box 834. If the patient repeats the right word, then the hearing health professional may mark a correct answer by clicking or pressing on the correct answer box 832. In some embodiments, the correct answer box 832 may include the word that was presented and possibly a picture associated with that word also. If the patient repeats the wrong word or does not answer, then the hearing health professional may mark an incorrect answer by pressing or clicking a wrong answer button 834. The test is concluded automatically by the speech discrimination module 308 when certain conditions are satisfied. In some embodiments, the test is concluded when a sufficient percentage of correct responses has been received (e.g., 85 percent), or a large enough sample has been obtained to give an accurate assessment.

Figure 9:
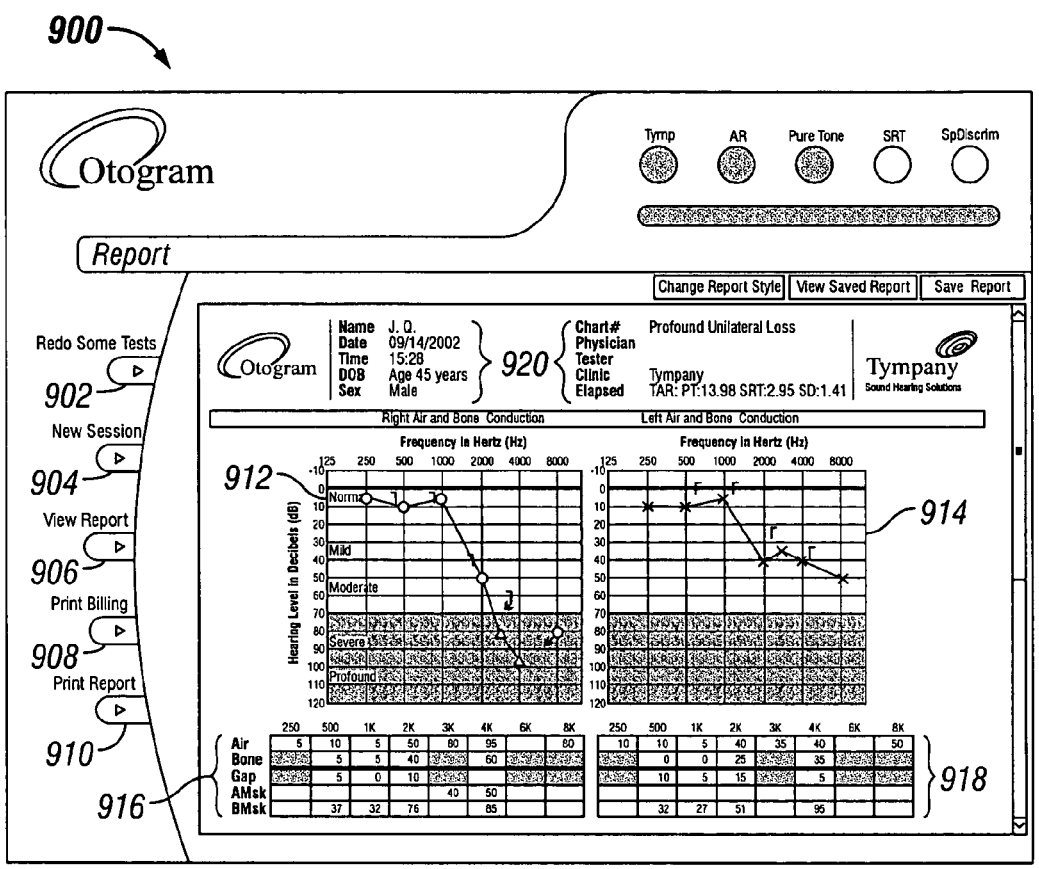
FIG. 9 illustrates an exemplary report generated by the computer-assisted diagnostic hearing test.

FIG. 9 illustrates an exemplary implementation of an on-screen report 900 generated by the hearing test 208 after the hearing related tests are completed. This screen may also be printed as a single page report. The report screen 900 generally includes all the relevant information that a hearing health professional should see. A plurality of buttons 902, 904, 906, 908, and 910 allows the hearing health professional to perform various tasks, such as redoing some of the test, starting a new session, viewing a report, printing the bills, printing the reports, and the like. The report screen 900 may present the results of the hearing test in a two-panel format, with the results of the right ear in one chart 912, and the results of the left ear in another chart 914. The charts 912 and 914 are computer-generated audiograms that reflect the patient's performance for a particular test (e.g., the air and bone conduction test). Other charts are available for other tests within a specific test session, as well as charts from multiple test sessions for a particular patient. The relevant data for each chart is also displayed (generally at 916 and 918), as well as some basic information (generally at 920), including the patient's name, date and time of the test, chart number, the physician, the tester or operator, the clinic, and the elapsed time for the test.

While the invention has been described with respect to a number of specific embodiments, those skilled in the art will recognize that the innovative concepts described herein can be modified and varied over a wide range of applications. For example, although the multimedia hearing test of the invention has been described in terms of a number of discrete modules, two or more of the modules may be combined to form one or more super modules, or one module may be divided into several sub-modules. Accordingly, the scope of the invention is not limited to any of the specific exemplary teachings discussed, but is instead defined by the following claims.

What is claimed is:

1. A multimedia diagnostic hearing test instrument for presenting a diagnostic hearing test to a patient by a hearing health professional in person, comprising:

an ambient noise module for graphically displaying an ambient noise level on a display unit that is physically connected to the diagnostic hearing test instrument, including an intensity level for one or more frequency components of the ambient noise;

a patient information module for displaying patient information on the display unit and allowing the hearing health professional to enter information for the patient in the diagnostic hearing test instrument and to select one of a plurality of hearing tests and an ear to test for the patient;

a pure tone module for allowing the hearing health professional to manually conduct, in person, a pure tone threshold test for the patient, including selecting an intensity level and frequency for a pure tone signal to be presented to the patient, the pure tone signal generated and presented by the diagnostic hearing test instrument to the patient through a transducer physically connected to the diagnostic hearing test instrument, the pure tone module further allowing the hearing health professional to manually or automatically set a masking level for the pure tone threshold test;

a speech reception module for allowing the hearing health professional to manually conduct, in person, a speech reception threshold test for the patient, including manually recording patient responses to the speech reception threshold test, the speech reception threshold test containing a plurality of words that are presented to the patient by the diagnostic hearing test instrument through the transducer; and a speech discrimination module for allowing the hearing health professional to manually conduct, in person, a speech discrimination test for the patient, including manually recording patient responses to the speech discrimination test, the speech discrimination threshold test containing a plurality of words that are presented to the patient by the diagnostic hearing test instrument through the transducer, the speech discrimination module further allowing the hearing health professional to manually or automatically set a masking level for the speech discrimination test;

wherein the pure tone module, the speech reception module, and the speech discrimination module are configured to store a patient response to a hearing test signal as and when manually indicated by the hearing health professional before a next hearing test signal is presented to the patient, and to generate a report illustrating a result of the respective tests thereof.

2. The diagnostic hearing test instrument according to claim 1, wherein the speech reception module further allows the hearing health professional to manually record a patient response to a word presented to the patient during the speech reception test by selecting a picture representation of the word displayed on the display unit.

3. The diagnostic hearing test instrument according to claim 1, wherein the speech discrimination module further allows the hearing health professional to manually record a patient response to a word presented to the patient during the speech discrimination test by selecting a picture representation of the word displayed on the display unit.

* * * * *